United States Patent [19]

Davies et al.

[11] 4,330,621

[45] May 18, 1982

[54] ASSAY FOR AMINOGLYCOSIDES

[75] Inventors: Julian E. Davies; Stephen Harford, both of Madison, Wis.

[73] Assignee: Wisconsin Alumni Research Foundation, Madison, Wis.

[21] Appl. No.: 181,270

[22] Filed: Aug. 25, 1980

[51] Int. Cl.³ .............................................. C12Q 1/48
[52] U.S. Cl. ..................................... 435/15; 435/193; 435/32
[58] Field of Search ............................. 435/15, 32, 33

[56] References Cited

U.S. PATENT DOCUMENTS 4,073,694  2/1978  Buda et al. ..................... 435/32 X Primary Examiner—Robert J. Warden
Attorney, Agent, or Firm—Howard W. Bremer

[57] ABSTRACT

A method for assaying a biological fluid, e.g. blood, for aminoglycoside content which includes rendering X-SH groups in the fluid insoluble and removing the insolubilized groups, adding acetyl-coenzyme A and a thiol detecting reagent to the solution and measuring its optical density, adding an enzyme characterized by high specific activity against aminoglycosides, measuring the optical density of the resulting solution and determining the difference in the optical densities.

12 Claims, No Drawings

ASSAY FOR AMINOGLYCOSIDES

CROSS REFERENCE TO RELATED APPLICATION

This invention is related to U.S. Ser. No. 93,758, filed Nov. 13, 1979 now abandoned and entitled "Method for Inactivating and Monitoring Antibiotics" in that the enzyme specifically disclosed and claimed in the referenced application, AAC(3)-IV, is eminently suitable for use in the process of the present invention.

BACKGROUND OF THE INVENTION

It is generally recognized that to be effective as antibacterial agents the plasma level of aminoglycosides must be maintained at above about 2 μg./ml. At concentration greater than about 10 or 12 μg./ml. these antibiotics exhibit a number of serious toxic side effects in that at such levels they can be ototoxic (auditory impairment) or nephrotoxic (renal function impairment), particularly with neonates and those exhibiting renal problems prior to treatment (see Smith et al, New England Journal of Medicine, Vol. 302, pp. 1106–1109 (1980)). In come rare cases these antibiotics have even been implicated in neural blockades. As a consequence, close monitoring of the serum aminoglycoside concentration is desirable so that the concentration can be generally kept within the 2–12 μg./ml. therapeutic range to allow for the effective treatment of bacterial infection while minimizing the possible toxic side effects.

Various assays have been developed and adopted to protect patients and to ensure effective antibacterial doses. Up to the present invention, however, such assays have been very expensive, inaccurate, laborious, require expensive equipment or require long assay times. In addition, such methods have tended to be specific to a particular aminoglycoside, have required the handling of radioisotopes or have been subject to interference by other compounds in the serum. Examples of such methods are: the bioassay, wherein the serum sample is tested microbiologically against sensitive bacterial strains through observation of zones of inhibition against bacterial growth; radioimmunoassay and radioenzymatic assays, which require specialized equipment and the handling of radioisotopes; latex agglutination, which is expensive and technically laborious; Emit method which requires purchase of an expensive kit and software package.

In addition to the above described assay methods a potential colorimetric method has also been known. This method finds a theoretical basis in the following equations:

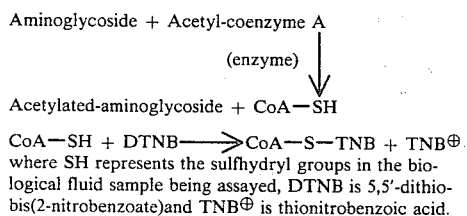

A.

$$\text{CoA-SH} + \text{DTNB} \longrightarrow \text{CoA-S-TNB} + \text{TNB}^\oplus$$ B.

where SH represents the sulfhydryl groups in the biological fluid sample being assayed, DTNB is 5,5'-dithiobis(2-nitrobenzoate) and TNB$^\oplus$ is thionitrobenzoic acid.

TNB$^\oplus$ is an intensely yellow colored compound which can be readily measured spectrophotometrically at 412 nm.

Although offering attractive possibilities, the method represented by the above schematic has not been applied to biological fluid samples, and particularly not serum (blood) samples, since DTNB will react with any sulfhydryl groups (proteins) represented by X—SH in the sample and since no enzyme was available which was characterized by a high specific activity against aminoglycosides and which would bring about reaction A rapidly.

THE INVENTION

The present invention provides an inexpensive, accurate, colorimetric method for assaying biological fluids which are characterized by the presence of X—SH groups, for aminoglycoside content.

The preferred method of this invention comprises: (1) treating the biological fluid to render the X—SH groups present insoluble and removing the insolubilized groups, (2) adjusting the remaining solution to a pH in the range from about 7.5 to about 8.2, (3) adding acetyl-coenzyme A and a thiol detecting reagent to the pH-adjusted solution, (4) measuring the optical density of the resulting solution, (5) adding an enzyme to the solution, which enzyme is characterized by a specific activity against aminoglycosides greater than about 50 μ moles product formed/min./mg. protein, (6) measuring the optical density of the resulting solution, and (7) determining the difference in the optical density values obtained.

In the foregoing method, the preferred method for insolubilizing the X—SH groups in the biological fluid is to treat the fluid with trichloracetic acid after which the insolubilized X—SH groups can be removed from the solution by filtration or centrifugation.

Alternatively, the X—SH groups (proteins) can be insolubilized with other acids, e.g. perchloracetic acid, by the use of heat, e.g. boiling the fluid for a few minutes, or by other known insolubilizing methods, or variations combinations of any of such methods.

After removal of the insolubilized X—SH groups the adjustment of the pH of the resulting solution can be readily accomplished by the addition of a suitable base as is well known in the art.

The thiol detecting reagent is preferably 5,5'-dithiobis(2-nitro-benzoate) because this compound is a visible color reactant, i.e. it permits the later spectrophotometric readings to be carried out in the visible light spectrum. Other thiol detecting reagents, such as 2,2'-dithiopyridine and 4,4'-dithiopyrindine, can be used but with such reagents the spectrophotometric values (optical densities) must be read in the ultraviolet spectrum.

Although any enzyme which is characterized by a specific activity in the range from about 50–200 μg moles of product formed/min./mg. protein can be used in the process, the preferred enzyme is AAC(3)-IV. As identified in accordance with universal nomenclature, AAC(3)-IV is an aminoglycoside acetyl transferase which acetylates the amino group at the 3 position of deoxystreptamine and it is identified as the IV type because of its substrate range. This enzyme can also be identified by the nomenclature acetyl coenzyme A: aminoglycoside-3-N-acetyl transferase. The enzyme is derived from the strain hereinafter referred to as UWBI (*E. coli*, ATCC 31958 American Type Culture Collection, 12301 Parklawn Dr., Rockville, Maryland 20852) which, in turn, can be derived from a naturally occurring isolate of a *Klebsiella pneumoniae* strain resistant to certain aminoglycoside antibiotics and which elaborates a new 3-N-acetyl-transferase. The organism *Klebsiella*

*pneumoniae* was selected on the basis of its broad antibiotic resistance. The generic material responsible for this resistance was recognized as the 3-N-acetyl transferase. This material was then taken as a plasmid-coded 3-N-acetyl transferase, given the identification JR 225 and incorporated into stock *E. coli* cultures; following transfer, a strain is chosen that retains aminoglycoside resistance with a minimum of other resistance determinants. *E. coli* was for safety and convenience. This *E. coli* strain, identified as JR225/W677, and hereinafter referred to as UWB1 has only one copy of the JR225 plasmid per cell, thus it has only nominal production capacity. A cloned derivative of UWB1, hereinafter referred to as UWB2 *E. coli,* ATCC31959 American Type Culture Collection, 12301 Parklawn Dr., Rockville, Maryland 20852); having activity many times greater than UWB1 was produced from plasmid DNA isolated from UWB1 by using UWB1 as a source of the JR225 fragments which were again incorporated into *E. coli.* The result is a multicopy plasmid strain that produces aminoglycoside-3-N acetyl transferase at a more rapid rate UWB1. The DNA is cut with restriction endonuclease Hind III and ligated in the presence of a multicopy vector. Transformation into an *E. coli* recipient and selection for aminoglycoside resistance provided strain UWB2. The cloned strain UWB2 is resistant to amino-glycosides, tetracyline and ampicillin.

As described in the related application cross-reference above the enzyme AAC(3)-IV was prepared in a 2 liter shaker flask containing 500 ml. of nutrient broth which was inoculated with 5 ml. of an overnight culture of UWB1 or UWB2 and incubated with shaking at 37° C. for 5-8 hours. The cells were harvested by centrifugation, washed with 0.1 M Tris buffer at a pH of 7.8. Cells were resuspended in 40 ml. of the same buffer and typically disrupted by passage through a French Pressure Cell or by sonic disruption. The crude extract was centrifuged at 20,000 xg for 30 minutes at 4° C. and the supernatant decanted and stored as the enzyme preparation. This preparation can be used with or without further purification.

About 30 seconds after the enzyme has been added in the above described process the optical density of the solution is determined and the difference between the two optical densities obtained is also determined. From the differences in the optical density values, the original concentration of aminoglycoside in the biological fluid can be calculated, or, if preferred, can be determined by comparison with a prepared standard curve all as is well known in the art.

The method of this invention offers several unique and unexpected advantages over the known method in the art. Thus, the method is fast (permitting about 10 samples to be assayed in about 10 minutes); no radioactivity is used; it is possible to run serum (blood) samples (impossible before because of interfering X—SH groups); equipment required is found as standard equipment in clinical laboratories; and it can be used to determine the presence and concentration of a number of aminoglycoside antibiotics, e.g. gentamicin, tobramycin, neomycin, netilmicin and kanamycin (thus dispensing with the need, as at present, for a distinct assay specific to each of such aminoglycosides).

Although the assay method of this invention is eminently suited to assaying for aminoglycosides in blood serum samples, it finds ready application to other biological fluids, e.g., saliva, urine, which may be characterized by the presence of interfering X—SH groups (proteins) and where a determination of the presence and/or concentration of an aminoglycoside is desired.

Inasmuch as many of the tools and reagents utilized in the asaay method of this invention are common to clinical laboratories where such assays are normally carried out, some of the chemical regents essential to conducting the assay and which may not be as readily available in clinical laboratories can be provided in convenient kit form. For example, the acetyl-coenzyme A, the enzyme, the thiol detecting agent and a reagent for insolubilizing X—SH groups lend themselves well to a kit assembly. Obviously other of the reagents utilized in the assay can also be included in the kit or fewer than those components specifically mentioned above can be included.

Having thus described the invention, what is claimed is:

1. A method for assaying a biological fluid sample for an aminoglycoside antibiotic comprising:
   (1) treating the biological fluid to render X—SH groups present in said fluid insoluble;
   (2) removing the insolubilized X—SH groups;
   (3) adjusting the remaining solution to a pH in the range from about 7.5 to about 8.2;
   (4) adding acetyl-coenzyme A and a thiol detecting reagent to said pH adjusted solution;
   (5) measuring the optical density of the resulting solution spectrophotometrically;
   (6) adding an enzyme characterized by a specific activity against aminoglycosides greater than about 50μ moles product formed/min./mg protein;
   (7) measuring the optical density of the resulting solution, and
   (8) determining the difference in the optical density values obtained in steps (5) and (7) whereby the original concentration of the aminoglycoside in the biological fluid sample can be determined.

2. The method of claim 1 wherein the biological fluid is blood.

3. The method of claim 2 wherein the enzyme added is AAC(3)-IV.

4. The method of claim 2 wherein the X—SH groups in the biological fluid are rendered insoluble by treatment with trichloracetic acid.

5. The method of claim 4 wherein the thiol detecting reagent is 5,5'-dithio-bis(2-nitrobenzoate) and the optical density is determined in the visible light spectrum.

6. The method of claim 4 wherein the thiol detecting reagent is 2,2'-dithio pyridine or 4,4'-dithio pyridine and the optical density is determined in the ultraviolet spectrum.

7. The method of claim 1 wherein the X—SH groups in the biological fluid are rendered insoluble by treatment with perchloracetic acid.

8. The method of claim 1 wherein the X—SH groups in the biological fluid are rendered insoluble by heating said fluid.

9. An assay kit for determining the aminoglycoside concentration in a biological fluid comprising, in packaged combination,
   (a) a container holding acetyl-coenzyme A,
   (b) a container holding an enzyme characterized by broad spectrum activity against aminoglycosides greater than about 50μ moles product formed/min./mg protein,
   (c) a container holding a thiol detecting reagent,
   (d) a container holding a reagent capable of insolubilizing X—SH groups present in biological fluids.

10. The assay kit of claim 9 wherein the enzyme is AAC(3)-IV.

11. The assay kit of claim 10 wherein the thiol detecting reagent is 5,5'-dithio-bis-2-nitrobenzoate.

12. The assay kit of claim 11 wherein the X—SH group insolubilizing reagent is trichloracetic acid.

* * * * *

UNITED STATES PATENT OFFICE
CERTIFICATE OF CORRECTION

Patent No. 4,330,621        Dated May 18, 1982

Inventor(s) Davies et al

It is certified that error appears in the above-identified patent and that said Letters Patent are hereby corrected as shown below:

Insert the following paragraph as the first paragraph of the Specification:

--The invention described herein was made in the course of work under a grant or award from the Department of Health and Human Services and Grant No. NSF PCM 79-13845 and IPA No. 0001 awarded by the National Science Foundation.--

Signed and Sealed this

Fourteenth Day of September 1982

[SEAL]

Attest:

GERALD J. MOSSINGHOFF

Attesting Officer    Commissioner of Patents and Trademarks